United States Patent [19]
Piez et al.

[11] Patent Number: 5,425,770
[45] Date of Patent: Jun. 20, 1995

[54] CALCIUM PHOSPHATE/ATELOPEPTIDE COLLAGEN COMPOSITIONS FOR BONE REPAIR

[75] Inventors: Karl A. Piez, Menlo Park; Bruce B. Pharriss, Palo Alto; George H. Chu, Sunnyvale; Thomas L. Smestad, Palo Alto; Diana Hendricks, Brea, all of Calif.

[73] Assignee: Collagen Corporation, Palo Alto, Calif.

[21] Appl. No.: 99,610

[22] Filed: Jul. 30, 1993

Related U.S. Application Data

[60] Division of Ser. No. 629,074, Dec. 17, 1990, Pat. No. 5,246,457, which is a continuation of Ser. No. 292,400, Dec. 30, 1988, abandoned, which is a continuation-in-part of Ser. No. 848,443, Apr. 4, 1986, Pat. No. 4,795,467, which is a continuation-in-part of Ser. No. 717,072, Mar. 28, 1985, abandoned.

[51] Int. Cl.⁶ ............................................. A61F 2/28
[52] U.S. Cl. ...................................... 623/16; 623/11; 623/66; 264/101; 264/122; 523/115
[58] Field of Search ............................ 623/11, 16, 66; 128/DIG. 8; 433/201.1; 523/113, 114, 115, 116; 264/101, 122

[56] References Cited

U.S. PATENT DOCUMENTS

| | | |
|---|---|---|
| 3,443,261 | 5/1969 | Battista . |
| 3,767,437 | 10/1973 | Cruz, Jr. . |
| 3,892,648 | 7/1975 | Phillips . |
| 3,949,073 | 4/1976 | Daniels . |
| 4,192,021 | 3/1980 | Deibig . |
| 4,314,380 | 2/1982 | Miyata et al. ............... 623/16 |
| 4,349,470 | 9/1982 | Battista . |
| 4,440,750 | 4/1984 | Glowacki . |
| 4,472,840 | 9/1984 | Jefferies . |
| 4,516,276 | 5/1985 | Mittlemeier . |
| 4,623,553 | 11/1986 | Ries et al. ........................ 427/2 |
| 4,627,982 | 12/1986 | Seyedin . |
| 4,743,229 | 5/1988 | Chu ................................ 604/110 |
| 4,776,890 | 10/1988 | Chu ................................ 106/161 |
| 4,795,467 | 1/1989 | Piez et al. . |
| 4,865,602 | 9/1989 | Smestad et al. ............... 623/16 |
| 4,888,366 | 12/1989 | Chu et al. . |
| 4,992,226 | 2/1991 | Piez et al. . |
| 5,035,715 | 7/1991 | Smestad et al. . |
| 5,123,925 | 6/1992 | Smestad et al. . |
| 5,231,169 | 7/1993 | Constantz et al. ........... 128/DIG. 8 |
| 5,246,457 | 9/1993 | Piez et al. ........................ 623/11 |

FOREIGN PATENT DOCUMENTS 0030583 6/1982 European Pat. Off. .
58-58041 10/1981 Japan .

OTHER PUBLICATIONS

Gross et al., "Bone-induction potential of mineralized collagen gel xenografts" *Oral Surg.* (1949) 49:21–26.

Hayashi et al., "Repair of experimental bone defect with a collagen block containing synthesized apatite" *Arch Ortho. Traumat. Surg.* (1982) 99:265–269.

Levy et al., "Healing potential of surgically-induced periodontal osseous defects in animals using mineralized collagen gel xenografts" *J. Periodontal.* (1981) pp. 303–306.

Trandafir et al., "Spongy structures of the osseous stroma type" *Chem. Abstr.* (1982) 82:407.

Lemons et al., "Inorganic and organic compound combinations for bone replacement" Biomaterials '84 Transactions, *Second World Congress On Biomaterials*, 10th Annual Meeting of the Society for Biomaterials Apr. 27–May 1, 1984, p. 6.

Lemons et al., "Synthetic hydroxylapatite and collagen combinations for the surgical treatment of bone" *Biomedical Engineering III* (Nov. 1984) pp. 13–16.

*Primary Examiner*—Paul Prebilic
*Attorney, Agent, or Firm*—Morrison & Foerster

[57] ABSTRACT

Processes for the preparation of compositions used in conductive bone repair are disclosed. The compositions contain a mixture consisting essentially of either a calcium phosphate particulate mineral component or particulate hydroxyapatite in admixture with atelopeptide reconstituted fibrillar collagen. The method is comprised of mixing a dispersion of the collagen and mineral, the latter which is present in dry particulate form, followed by molding and drying the composition in a mold to obtain a dried composition.

1 Claim, 1 Drawing Sheet

CALCIUM PHOSPHATE/ATELOPEPTIDE COLLAGEN COMPOSITIONS FOR BONE REPAIR

The application is a division of 07/629,074 filed Dec. 17, 1990, now U.S. Pat. No. 5,246,457, which is a continuation of 07/292,400 filed Dec. 30, 1988, now abandoned, which is a continuation-in-part of 06/848,443 filed Apr. 4, 1986, now U.S. Pat. No. 4,795,467, which is a continuation-in-part of 06/717,072 filed Mar. 28, 1985, now abandoned.

TECHNICAL FIELD

This invention relates to the field of hard tissue repair. Specifically, it relates to the use of mixtures of atelopeptide reconstituted fibrillar collagen with hydroxyapatite or calcium phosphate mineral preparations in bone grafts.

BACKGROUND ART

The general notion of using mixtures or combinations of collagen protein and bone minerals in effecting hard tissue repair has been known for some time. As bone itself is comprised of these minerals, along with collagen, it seemed promising to utilize this combination. However, implementation of this concept has not proved to be as simple as might have been supposed. First, it has been difficult to obtain a preparation which has the correct physical properties to provide a support matrix for bone in-growth so as to result in a successful repair. Second, unless the proteinaceous component was derived from tissue of the same individual who is the recipient of the implant, inflammatory responses are commonplace as a result of the immunogenic character of the implant. This problem is not entirely obviated by using collagen derived from the same species, but performance is improved over that resulting from use of collagen from, for example, bovine or porcine sources in humans. Thus, the form of the collagen used is critical to the success of the implant. The form of the mineral component is not critical, except the resulting mixtures must have handling properties suitable for the indications.

Reports of attempts to use the collagen/mineral combination are numerous. For example, Lemons, J., et al., reported at the Second World Congress of Biomaterials in Washington, D.C., 27 Apr.–1 May 1984, on attempts to utilize collagen along with commercial hydroxyapatite and calcium phosphate to repair artificially created lesions in rabbits. The use of these mixtures did not result in reunion of the lesions. A control experiment using fresh autogenous bone, however, was successful in producing a union. Similarly, Levy, P., et al., *J Periodontal* (1981), 52:303–306, were unsuccessful in their attempts to utilize collagen/mineral gel implants to repair intra-bony defects in root canals of canine or monkey teeth. Gross, B. C., et al., *Oral Surg* (1980), 49:21–26, reported limited success in using mixtures of reconstituted lyophilized calfskin collagen in admixture with a hydroxyapatite preparation to induce bone growth through subperiosteal implants in monkeys. Various others lave reported use of forms of collagen which clearly contain telopeptides, a major source of immunogenicity of collagen, in combination with minerals in bone repair. See, for example, Hayashi, K., et al., *Arch Orthop Traumat Surg* (1982) 99:265–269; Battista, U.S. Pat. No. 4,349,470 (using a hydrated gelatin); Cruz, Jr., U.S. Pat. No. 3,767,437 (using a calcium-precipitated form of collagen); and Battista et al., U.S. Pat. No. 3,443,261 (utilizing, in addition to calcium phosphate, a "new form" of collagen which contains microcrystals of aggregated tropocollagen units.

Miyata et al., U.S. Pat. No. 4,314,380, utilized a mineral backbone prepared directly by treatment of animal bone to remove all organic materials, which was then coated with an atelopeptide collagen. Japanese Application J58/058041, published 6 Apr. 1983, discloses a spongy porous calcium phosphate material having pores treated with atelopeptide collagen. The collagen derives from collagen-in-solution having a concentration of not more than 2% by weight. The Japanese application reports the advance of osteoblasts into the pores of the material and new bone growth. European Patent Application, Publication No. 030583, published 24 Jun. 1981, discloses use of COLLAGENFLEECE ® in admixture with hydroxyapatite in bone repair. This collagen material is a commercial product, is obtained from animal hide by proteolytic digestion, and is lyophilized and sterilized by gamma-irradiation. This collagen preparation forms a soft membrane-like material but does contain telopeptides and is partially degraded by the processing.

In summary, there have been numerous attempts to use combinations of calcium phosphate mineral components and collagen in various forms of bone defect repair with mixed success. It is clear that the art contains no perfect composition which can be relied upon to provide satisfactory results in a predictable manner in connection with a specific process. A reproducibly effective preparation for encouraging bone in-growth was, until the present invention, lacking in the art.

DISCLOSURE OF THE INVENTION

The present invention provides a composition containing a collagen and a calcium phosphate mineral component which provides a successful support for ingrowth of new bone tissue. The mineral component can be one of a variety of bone-compatible calcium phosphate salts such as hydroxyapatite (HA) or tricalcium phosphate (TCP); the collagen is a specific form: reconstituted fibrillar atelopeptide collagen. The mixture can be supplied in either wet or dry form, and can be, if desired, cross-linked to a predetermined extent. The physical and handling properties of the mixtures can be improved by a number of curing processes, including heat, maturation of the wet mixture, and specific cross-linking. The composition is effectively used in grafting procedures both in connection with skeletal bone and in periodontal procedures.

In other aspects, the invention is directed to methods of bone augmentation or repair using the compositions of the invention and to a method of coating the pores of a calcium phosphate mineral porous block with collagen.

In still another aspect, the invention is directed to certain preferred specific compositions and methods.

MODES OF CARRYING OUT THE INVENTION

Nature of the Compositions

Figure 1:
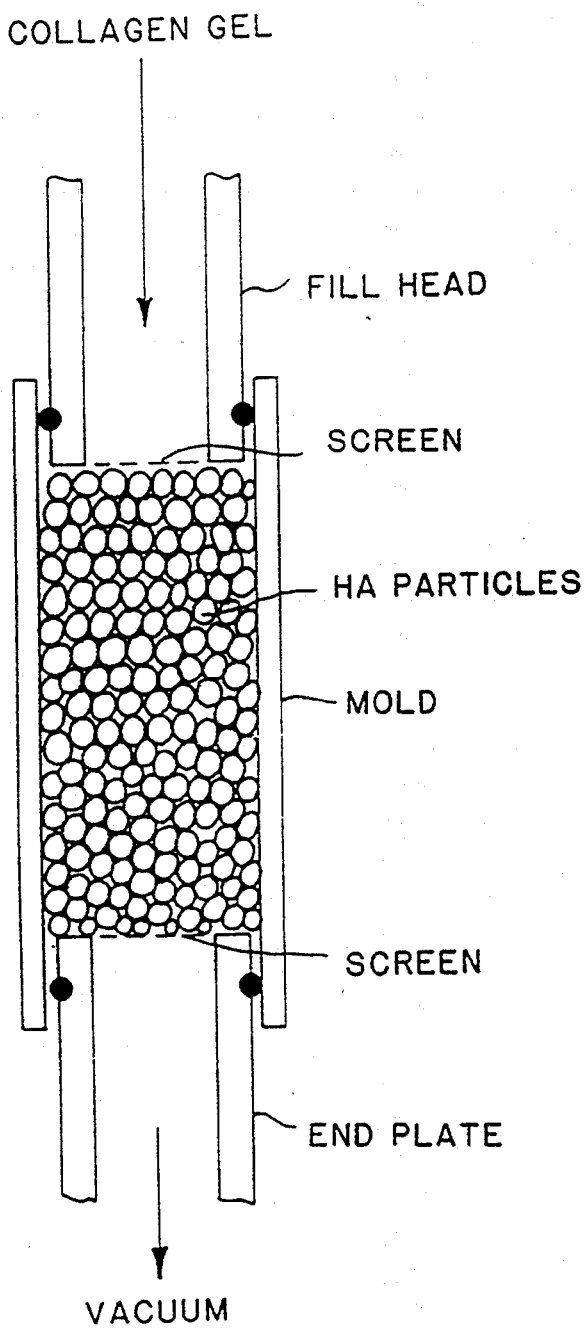
FIG. 1 shows a method to prepare a collagen-coated mineral support block.

The present invention is directed to compositions for conductive repair of bone. The compositions and methods of the invention provide a support matrix on which new bone growth can occur, but do not provide factors which are responsible for "inductive" bone growth or repair. In general, "conductive" repair of bone refers to provision of suitable conditions for the self-generated ingrowth of bone while "inductive" repair, in addition to providing this environment, also supplies bioactive molecules which stimulate the progenitor cells to differentiate and grow. The compositions and methods of this invention do not include any biologically active drugs, such as osteogenesis factors or cartilage-inducing factors.

The compositions of the invention can use a variety of calcium phosphate mineral component materials. As used herein, "calcium phosphate mineral" materials refers to those materials composed of $Ca^{+2}$ and phosphate ions, regardless of the microstructure protonation status of the phosphate, or extent of hydration. Calcium phosphate mineral materials include a variety of forms, such as the commercially available forms of tricalcium phosphate, for example, SYNTHOGRAFT® tricalcium phosphate, or of hydroxyapatite such as PERIOGRAF®, ALVEOGRAF®, INTERPORE®, ORTHOMATRIX® HA-1000™, or ORTHOMATRIX® HA-500 ™ hydroxyapatite particulate preparations. The hydroxyapatite or tricalcium phosphate may also be prepared by known methods, such as those disclosed by Termine et al., *Arch Biochem Biophys* (1970) 140:307–325, or by Hayashi, K., et al., *Arch Orthop Trauma Surg* (supra). In any event, the mineral is supplied as a powder of appropriate mesh. Preferred particle sizes are in the range of 100–2000 microns. While the mineral content of bone could be harvested and purified for this purpose, more economically prepared and controlled compositions are preferable, both as a matter of cost and of quality. If solid blocks are desired, these are prepared from the particulate form as described below.

The collagen component of the composition is critical to its efficiency. Numerous forms of collagen have been prepared and they differ in their physical properties as well as in their biocompatibility. It does not appear, however, that the particle size is relevant within the range of diameters over which a mixture will be a solution, colloid, or suspension, and in order to permit use of a single generic term, "collagen dispersion" is used herein to refer to a collagen preparation in aqueous medium in which the collagen particle size is not specified—i.e., the preparation may be a solution, suspension, or gel.

Native collagen consists mainly of a triple helical structure containing repeating triplet sequences composed of glycine linked to two additional amino acids, commonly proline and hydroxyproline. Native collagen contains regions at each end which do not have the triplet glycine sequence, and thus do not form helices. These regions are thought to be responsible for the immunogenicity associated with most collagen preparations, and the immunogenicity can be mitigated by the removal of these regions to produce "atelopeptide" collagen. This can be accomplished by digestion with proteolytic enzymes, such as trypsin and pepsin. The non-helical telopeptide regions are also responsible for natively occurring cross-linking, and atelopeptide collagen must be cross-linked artificially if cross-linking is desired.

Naturally occurring collagens have been subclassified into about ten types, depending on the amino acid sequence in the individual chains, the carbohydrate content, and the presence or absence of disulfide cross-links. The most common subtypes are Type I, which is present in skin, tendon, and bone, and which is made by fibroblasts; and Type III, which is found primarily in skin. Other types reside in specialized membranes or cartilage, or at cell surfaces. Types I and III contain similar numbers of amino acids in their helices and have a high degree of homology; however, Type III, but not Type I, contains two adjacent cysteines at the C-terminal ends of the triple helix, which are capable of forming interchain cross-links.

Therefore, collagen preparations may differ from each other by virtue of their initial compositions, which is a function of their origin, or by virtue of their modes of preparation. Collagen derived from bone, for example, contains exclusively Type I collagen; while collagen derived from skin also contains Type III. Also, the process of preparation may or may not remove the telopeptides. Thus both unaltered and "atelopeptide" collagen are possible. Cross-linking may be effected deliberately or accidentally. Sterilization by gamma-irradiation or by high heat may result in cross-linking without control of extent or nature and results in partial degradation of the triple helix; deliberate cross-linking may be carried out by a variety of means, including treatment with glutaraldehyde. Differences arising from perhaps more subtle causes are perhaps the result of variations in the details of the preparation procedure. For example, the collagen may be solubilized and reprecipitated, or may simply be finely divided and kept in suspension. When the solubilized material is reaggregated, the aggregation may be done in ways so as to form non-specifically bonded solids, or the collagen may be reconstituted into fibers which simulate the native form. Also, of course, the degree of purity may vary.

As used herein, "free from impurities" or "purified" as regards collagen preparations refers to those impurities which are normally associated with collagen in its native state. Thus, collagen prepared from calfskin is free from impurities when other components of calfskin have been removed; that from bone when other components of bone are eliminated.

"Reconstituted" collagen refers to collagen which has been disassembled into individual triple helical molecules, with or without their telopeptide extensions, brought into solution and then regrouped into "fibrillar" forms. In this form, the fibrils consist of long, thin collagen molecules staggered relative to one another by multiples of about one-fourth their length. This results in a banded structure which can be further aggregated into fibers.

Collagen which is "substantially free from cross-linking" refers to collagen which has had the atelopeptides removed, and thus lacks the native capacity for cross-link formation. These preparations remain substantially cross-link free if not deliberately cross-linked by, for example, being treated with glutaraldehyde or subjected to treatment imposing a spurious form of linkage—for example, treatments often used for sterilizing purpose, such as high temperature and gamma-radiation The product produced by the present invention may be processed aseptically, thereby resulting in a sterile product. Alternatively, the product may be prepared and thereafter sterilized by gamma-ray irradiation, as, for example, in the related U.S. patent application Ser.

No. 06/928,306, filed 6 Nov. 1986, the contents of which are herein incorporated by reference.

The collagen suitable for use in the invention is a purified atelopeptide fibrillar reconstituted collagen.

One suitable collagen preparation which meets these specifications is an atelopeptide collagen which is reconstituted into fibrillar form and supplied as a dispersion of 5–100 mg/ml, preferably around 50–70 mg/ml. Such dispersions as ZYDERM® Collagen Implant (ZCI), which is commercially available in preparations containing 35 mg/ml collagen or 65 mg/ml collagen in saline, manufactured by Collagen Corporation, Palo Alto, Calif., are appropriate. For use in the compositions of the inventions, the ZCI or other collagen dispersions are used without lidocaine or other sedative drugs. As used herein, "ZCI" refers to the aqueous collagen dispersion, rather than to the collagen component per se.

The compositions of the invention contain 50–85% by weight of calcium phosphate mineral component, preferably 65–75% mineral component, and the balance is a collagen dispersion such as ZCI. In terms of the mineral/collagen ratio (excluding the aqueous dispersion component), the mixtures are 60–98% mineral, preferably 75–98% mineral and the rest collagen. The composition may be prepared simply by mixing the two components into a cohesive mass and then loading the mixture into an appropriate container which is packaged directly to supply a "wet" product. Alternatively, the mixture is cast into a desired shape (e.g., blocks, squares, sheets) and then lyophilized or air dried and packaged to provide a "dry" product. The degree of dryness obtained is, of course, arbitrary, since both "wet" and "dry" forms are usable. However, as used herein, the "dry" form refers to mixtures containing <1.0% moisture by weight. For lyophilized material, substantially all moisture is removed. The dry material is rigid and can be cut with a sharp instrument.

If cross-linking is desired, glutaraldehyde to a level of 0.001–0.1% is used to treat the dry product after drying, or high temperature treatment is applied to the dry product. For cross-linking the wet product, glutaraldehyde may also be used and the excess then removed by washing.

Additional components may be added to the composition of the invention if desired, including bone marrow, blood, and saline- The percentages given above refer to the composition of the collagen/mineral mixture only; this combination mixture forms from 10–100% by weight of the composition supplied to the subject.

An alternative form of the composition comprises a porous but rigid mineral block shaped as desired for the application and coated with collagen from a collagen dispersion that has been infiltrated into the pores. Porous blocks of hydroxyapatite and/or tricalcium phosphate are known and available. Blocks are made from the powdered form by compacting in the presence of liquid and then drying. The compositions of the invention which comprise this rigid form are conveniently and preferably prepared as described hereinbelow.

Methods of Use

The resulting composition is used to augment bone and fill bony defects, for example, periodontal bony pockets, tooth extraction sockets, and jaw cysts.

The present invention has several targeted therapeutic applications. These applications include traumatic (fresh) fractures, delayed unions, non-unions, spinal fusions (in particular, scoliosis, degenerative disks, low back pain, etc.), bone cyst repair, cranial facial augmentation, and implant fixation (orthopedic and dental). One skilled in the art will readily see numerous possible applications for the material. For example, for a cranial facial therapeutic application, a custom implant may be formed which is specifically tailored to the patient. Alternatively, "generic" implants may be made in a variety of sizes and fitted to the particular patient. One important example of onlay procedures includes alveolar ridge augmentation. The procedures for this surgical implantation are known in the art. For alveolar ridge augmentation, the composition is inserted under the periosteum in places where augmentation is desired.

The foregoing examples demonstrate that the term "repair" in the present invention should be broadly interpreted to include a variety of applications in which bone growth is required. The compositions are implanted, either directly or manually or by injection into an area into which bone growth is desired. The "implant" should be in physical contact with living osteogenic cells in the adjacent tissue so that the matrix supplied can "conduct" the growth of bone into the desired space.

In orthopedic and reconstructive applications in general, mineral in the form of porous blocks may also be indicated, particularly where the graft must bear stress. The collagen-impregnated blocks may be implanted or set in place by standard surgical techniques.

Preparation of Rigid Block Forms

A typical procedure for preparing a mineral powder or block impregnated with collagen is shown in FIG. 1. For use in this embodiment HA is preferred. A mold of the desired shape is fabricated of a suitable material such as stainless steel. The mold is made up of a body and two removable, screened ends (the end plate and fill head). Each end has a tubuation in order to attach a tubing through which the collagen gel will flow. The screens are of a sufficiently small size to retain mineral particles, yet permit the flow of the collagen gel.

The end piece is attached to the mold, and the mold filled with mineral as a powder or a block to the desired volume. The remaining end piece (the filling head) is lowered to the upper level of mineral to seal the mold. The collagen dispersion, preferably a gel, is pumped into the mold until flow is detected from the outflow; the mold and mineral may be evacuated to assist injection and minimize air entrapment. The conglomerate may optionally be compressed before removing the head plates and ejecting the implant.

The collagen gel content of composites prepared following the foregoing method are limited to the void space between the mineral particles. For example, the use of 20–40 mesh mineral will yield a ratio of 25:75 collagen to mineral by weight. The resulting material is more rigid with increased mineral content.

The foregoing method is, of course, not limited to preparations of the invention, but can be used to provide collagen coated pores in calcium phosphate mineral blocks for a wide range of collagen preparations.

The solid block forms of the mixtures of the invention, whether prepared by compaction of the mineral followed by collagen coating or by drying a collagen/mineral mixture, may be cured to obtain greater integrity under stress by various curing treatments.

Preferred Embodiments

Several specific formulations represent preferred embodiments of the present invention.

In a first preferred embodiment, the composition is a mixture of about 92-96%, preferably about 94% mineral as a mixture of hydroxyapatite and tricalcium phosphate and about 4-8%, preferably about 6% atelopeptide reconstituted fibrillar collagen. The mineral composition is preferably about 30-45%, most preferably about 40% beta-tricalcium phosphate and about 55-70%, most preferably about 60% hydroxyapatite. This mixture is prepared from dry particulate mineral and a dispersion of collagen in water or buffer, preferably at about 20-70 mg/ml, and may be formulated shortly before application or may be molded and lyophilized. If mixed shortly before application, the collagen/mineral mixture can also be supplemented by bone marrow removed from the patient being treated. Generally, the collagen/mineral mixture is mixed with the marrow in a ratio of mixture:marrow by weight of about 6:1-3:1, preferably 5:1-4:1. If the molded and lyophilized material is used, this, too, can be used as such, or as preferred, can be cured to increase its rupture strength, for example by heating to about 75° C. for 12 hours at less than 12% relative humidity. If no further sterilization is conducted, the original mixture must be produced aseptically and treated under aseptic conditions. Alternatively, the lyophilized product may be rehumidified and packaged and sterilized using gamma irradiation.

In a second preferred embodiment, the composition is a mixture of about 87-91%, preferably about 89% hydroxyapatite and tricalcium phosphate (as above) and about 9-13%, preferably about 11% atelopeptide reconstituted fibrillar collagen. The mixture is prepared as above, preferably using a collagen suspension at about 65 mg/ml and may also be molded and dried, preferably under ambient pressure conditions and at about 37° C. If prepared aseptically, the mixture can be used as such, and can be further processed by heat curing, for example, at about 75° C. for twelve hours at 48% relative humidity or can be rehumidified and sterilized by gamma irradiation.

In a third preferred embodiment, the composition is a mixture of about 95-99%, preferably about 97% hydroxyapatite and about 1-5%, preferably about 3% atelopeptide reconstituted fibrillar collagen. The mixture is prepared as above, preferably using a collagen dispersion at about 65 mg/ml, and is preferably molded and dried under sterile conditions. For the mineral component in this embodiment, however, particles of hydroxyapatite alone are used. Tricalcium phosphate is substantially absent. If mixture, molding and drying (under ambient conditions at about 37° C.) are conducted under aseptic conditions, the resulting product can be packaged aseptically, and, if desired, hardened by heat curing. Alternatively, the dried material can be rehumidified for packaging and sterilized by gamma irradiation.

Curing Processes

In one process, a heat-curing process, the air-dried composite, in block form, which must contain less than 1% moisture before treatment, is heated to 60°-120° C., preferably 75°-90° C., for 4-168 hours, preferably 6-72 hours. The curing may take place either in open or closed containers. The resulting blocks are considerably more rigid and resistant to pressure than the uncured materials.

In an alternate curing process, longer times, but lower temperatures, are employed. In one such process, the composite, while still wet, is cured in a moistened state in a closed container for 1-10 days at 37° C., and then dried at ambient temperature-37° C. to dryness. This material is relatively rigid, but can be further cured using the heat-curing process above.

In still another curing method, the mixture is subjected to cross-linking while still in a wet state and then dried at ambient temperature-37° C. to dryness, optionally followed by heat curing. For the cross-linking, one usable procedure is to incubate the wet block at 37° C. for 1-10 days, preferably 1-2 days, in the presence of a vaporized cross-linking agent such as the vapors of glutaraldehyde. This process is most conveniently conducted in a closed container to confine the vapors. After suitable cross-linking, the composite is dried at ambient-37° C. until a moisture content of less than 1% is achieved.

In the alternative, cross-linking can be achieved by soaking the wet mixture in the cross-linking reagent solution. Such a solution contains, for example, 0.001-1%, preferably 0.001-0.005% glutaraldehyde or formaldehyde. Treatment lasts for 4-48 hours, preferably around 24 hours, and is conducted at ambient temperature. After washing with sterile water to remove excess cross-linking agent, the composite is dried at ambient temperature-37° C., as above.

The results of the foregoing curing processes are, in general, superior values of the compressive modulus or of rupture strength measured in Newtons per square centimeter ($N/cm^2$).

Cranial Onlay Model

The compositions of the invention were tested in a cranial onlay model. Rats, 8-10 weeks old, were anesthetized and the scalp reflected. A coronal incision was made in the periosteum, which was then elevated to form a tent sufficient to accommodate placement of a single implant directly on the bony surface of the cranium. Each rat received one implant of experimental or control material, and the periosteum was drawn over the implant and the scalp repositioned and sutured. The implant sites were evaluated by x-ray and histology at 4, 8, and 16 weeks post-implantation.

EXAMPLES

The following examples serve to illustrate but not to limit the invention.

Example 1

ZCI/Hydroxyapatite

A mineral/collagen preparation was obtained by mixing 65 parts by weight of PERIOGRAF® hydroxyapatite with 35 parts by weight of ZYDERM® collagen implant (ZCI) (65 mg/ml) without lidocaine. (Since the ZCI is 6.5% collagen in saline, the final composition is 65 parts HA, 2.3 parts collagen (0.065×35) and 32.7 (35−2.3) parts saline, all by weight.) In terms of the dried components, the mixture is 65 parts HA and 2.3 parts collagen by weight, or 3% collagen/97% mineral by weight.

To obtain the wet composition, the mixture was thoroughly mixed, and 0.4 ml portions placed into a widebore syringe for direct use. To obtain the dry preparation, portions measuring 0.55 ml were placed in a widebore syringe and the plunger removed to permit the mixture to dry. The mixture was dried under a Laminar Flow Hood (LFH), and the plunger replaced for convenient packaging.

Both the wet and dry compositions were used in the cranial onlay model. Thirty-six rats were used in the study; 12 were supplied implants of the dry mixture, 12 of the wet, and 12 hydroxyapatite alone as a control.

After 4 weeks, x-ray films showed that the air-dried implants held their shape and remained in a mound after placement. Wet implants or hydroxyapatite alone spread over the surface of the cranial vault. The hydroxyapatite particles averaged 3-4 layers in all types of implants.

Air-dried implants showed more extensive bone formation than wet implants, frequently extending from the base of the implant to the distal border, while osteogenic activity in wet implants was more uneven and generally limited to less than 50% of the thickness. Hydroxyapatite alone showed bone formation only around the first layer of particles adjacent to the skull. In all cases, bone formed in direct contact with the hydroxyapatite particles with no intervening tissue. Thus, fusion between new and preexisting bone occurred in all implants. However, bone marrow differentiation and the amount of bone was always greater in the air-dried implants according to histological studies. No inflammation was shown except for sequestering and encapsulation of hydroxyapatite particles not involved in layers contiguous to new bone formation.

Thus, the collagen composites increased the rate of bone fixation over hydroxyapatite alone. Air drying of composites also favors more extensive bone formation.

Example 2

A. Effect of Curing

The mixtures as prepared in Example 1 (except that ORTHOMATRIX HA-1000 ® was used as the mineral component), wet or dry, as specified, were subjected to curing processes to ascertain the effect on rigidity. The dry material (less than 1% moisture) showed a compressive modulus ( ) of 1.25 N/cm$^2$. This could be improved by subjecting the dry material to curing at elevated temperatures for various lengths of time. The results in Table 1 indicate that optimum results are achieved by heating at higher temperatures and longer times.

TABLE 1

| Temp. (°C.) | Time (hrs) | Compressive Modulus (N/cm$^2$) |
|---|---|---|
| 60 | 72 | 3.35 |
| 60 | 96 | 3.87 |
| 60 | 120 | 4.0 |
| 60 | 144 | 4.1 |
| 80 | 24 | 5.7 |
| 80 | 48 | 6.3 |
| 80 | 72 | 6.3 |
| 80 | 96 | 7.0 |
| 80 | 120 | 7.6 |
| 80 | 144 | 10.5 |
| 80 | 168 | 11.0 |
| 100 | 4 | 4.1 |
| 100 | 16 | 6.1 |
| 100 | 26 | 6.75 |
| 100 | 48 | 7.55 |
| 120 | 10 | 14.3 |
| 120 | 26 | 16.7 |

An improved compressive modulus could also be achieved using a cross-linking process in solution conducted at 20° C. for 24 hours. The improvement was dependent on the cross-linking agent concentration; results for various concentrations of glutaraldehyde under these conditions are shown in Table 2.

TABLE 2

| Glutaraldehyde Conc. (%) | Compressive Modulus ($\Sigma$) |
|---|---|
| 0.001 | 13.9 |
| 0.002 | 16.15 |
| 0.003 | 18.0 |
| 0.004 | 21.0 |
| 0.005 | 24.15 |
| 0.01 | 32.0 |

Even simple incubation at 37° C. before drying was able to increase the compressive modulus considerably. A sample of the mixture in Example 1 was incubated at 37° C. for 168 hours before drying at ambient temperature to a moisture content of <1.0%. This composite exhibited a compressive modulus of 6.15 N/cm$^2$, as compared to the 1.25 N/cm$^2$ shown by the mixture dried immediately after mixing.

B. Compressive Modulus Measurement

Compressive modulus is measured on a commercially available Instron Universal Tester, model 4202, attached to a Hewlett Packard X-Y Plotter. The blocks of material to be tested are wetted in 0.9% NaCl solution for 5-24 hours before testing. The instrument is calibrated and the moistened block is measured and placed on the instrument platform. The lead is brought down to just above the block, the chart reset, and the pressure applied to the block. The plotter generates a curve plotting centimeters on the X axis and Newtons on the Y axis. A tangent is drawn through the curve through the five Newton point to intersect the X axis; a vertical line is dropped from the tick, which indicates block crumbling, to the X axis. The height of this vertical line is determined, and divided by the centimeter distance generated by the difference in points of intersection of the vertical and tangent line and by the width of the block. The strength is normalized by dividing the length and height of the block.

The compressive modulus may also be determined on other compressive modulus measuring devices as is generally known in the art.

C. Rupture Strength Measurements

The strength of the composition can be measured, alternatively, by determining the "rupture strength" of the material, a quantity which is also measured in Newtons/cm$^2$. Typical rupture strength of the compositions of the invention are above 0.15 N/cm$^2$, and preferably above 0.3 N/cm$^2$. The value of the rupture strength can be conveniently determined as follows:

Rectangular blocks of the collagen mineral preparation to be tested are affixed at either end to tape strips. The blocks are then soaked in PBS in shallow covered containers overnight and then clamped into the pneumatic grips by virtue of the attached tabs vertically in an Instron Universal Tester model 4202 attached to a Hewlett Packard X-Y Plotter. Rupture strength testing is according to the protocol associated with the apparatus. In the protocol, the block is extended at 1 cm/minute until it ruptures. The plotter generates a curve showing extension in centimeters on the X axis and force in Newtons on the Y axis. The data obtained show the peak force and the extension at the point of rupture. The rupture strength is then calculated as the force at rupture in Newtons divided by the cross-sectional area of the block measured in $cm^2$.

Other methods to measure rupture strength are known in the art, and could be substituted for the foregoing.

Example 3

A mineral/collagen preparation was obtained by mixing 5 ml of reconstituted atelopeptide fibrillar collagen (FC) at 65 mg per ml, supplied as ZYDERM® Collagen Implant without lidocaine, with 5 g of a mixture of 35% beta-tricalcium phosphate/65% hydroxyapatite, the mixture having a void space of about 20–40% and a mean pore size of 500 microns. The collagen/mineral mixture was prepared by simple mixing of the materials. This material can be used per se, and can be prepared by the attending physician. In addition, two ml of bone marrow may be mixed with the above collagen/mineral mixture to form an implant preparation. The hydroxyapatite/tricalcium phosphate to collagen ratio is 15:1 by dry weight so that the dry components are about 94% TCP/HA and about 6% FC by weight.

Example 4

A mineral/collagen preparation having a dry weight % of TCP/HA of about 94% and 6% FC was obtained by mixing 72.7 parts by weight of FC at 25 mg/ml with 27.3 parts by weight hydroxyapatite and tricalcium phosphate. The collagen was supplied as a dispersion of atelopeptide fibrillar reconstituted collagen without lidocaine, and the HA/TCP mixture was approximately 35% beta-TCP and about 65% HA as described in Examples 3 and 5.

The mineral and FC components were mixed, placed into a mold, and lyophilized. If mixture of sterile products is done aseptically, the aseptic processed product can be further processed aseptically and packaged aseptically. One preparation was made by heat curing the aseptically produced material at 75° C. for twelve hours at a relative humidity of <12%. The heat cured material has a rupture strength of 0.3 $N/cm^2$. The product is then aseptically packaged for use.

Alternatively, the lyophilized material was rehumidified prior to packaging and then sterilized by gamma ray irradiation to obtain a sterilized product with a rupture strength of 0.3 $N/cm^2$.

Example 5

A mineral/collagen preparation was obtained by mixing 65 parts by weight of ZYDERM® Collagen Implant (ZCI 65 mg/ml) without lidocaine and 35 parts by weight of a mixture containing 35% beta-TCP/65% HA with a void space of about 20–40% and mean pore size of 500 microns. The resulting mixture, which had a gel-like consistency was loaded into a mold and dried at ambient pressure at 37° C. to dryness. The resulting composite was then aseptically processed by heat curing or sterilized with gamma irradiation to provide a "terminal sterilized" product.

A. Aseptic Process Product

To produce an aseptically processed product, the dry hydroxyapatite/tricalcium phosphate/collagen composite was heat cured in an aseptic environment at 75° C. for 12 hours at a relative humidity of 48%. This dry heat-cured composite has a rupture strength of 0.3 $N/cm^2$.

B. Terminal Sterilized Product

The dry form of hydroxyapatite/tricalcium phosphate/collagen composite was rehumidified, packaged, and gamma-irradiated for sterilization and cross linking to provide a product with a rupture strength of 0.3 $N/cm^2$.

Example 6

Efficacy of the Compositions

Eighteen adult (2–5 years old) mongrel dogs with an average weight of 31 kg were operated unilaterally on the forelimb to create a mid-diaphyseal defect in the ulna using a model similar to that described by Heiple et al. *J Joint Bone Surg* (1963) 45A:1593–1612. In each case the contralateral ulna was left intact to serve as the control for mechanical testing. The dogs were randomly divided into three groups; 6 dogs in Group I received 2.5 g HA/TCP mixed with 4.5 ml FC mixed as described in Example 5 in the gel form (obtained by direct mixing, prior to molding and lyophilization), yielding 5.6 cc of implant; in the 6 dogs in Group II, this mixture was additionally mixed 4:1 by volume with autogenous bone marrow (BM) and the remaining 6 dogs in Group III the defects were filled with a 4:1 mixture by volume of FC and BM without ceramic.

Prior to surgery, each dog was weighed, a blood sample was drawn and a radiograph taken to verify skeletal maturity.

Surgical procedures and animal care were performed in accordance with NIH regulations. Anesthesia consisted of appropriate premedication, intubation, and general anesthesia with Methoxyflurane. Antibiotic prophylaxis was intravenous Cefazolin sodium preoperatively and postoperatively.

The left forelimb was prepared and draped for standard aseptic surgery utilizing sterile technique. The mid-portion of the left ulna was exposed by subperiosteal dissection, preserving the periosteal cuff, through a postero-lateral approach. A 2.5 cm segment of the ulna was excised using a water cooled oscillating saw; the distal cut was placed 6 cm proximal to the styloid of the ulna. The ulna was stabilized with a 2 mm intramedullary pin.

The appropriate implants were mixed and finger packed into the defect. Sufficient material was placed to fill the periosteal tube and approximate the diameter of the intact ulna. The periosteum, muscle, and skin were closed in layers and sterile dressings were applied. For the first two days postoperatively the animals were kept in a climatically controlled recovery room and were permitted to bear weight as tolerated. Thereafter they were maintained in open air kennels, and allowed activities as tolerated.

All animals were euthanized 24 weeks postoperatively with an overdose of intravenous barbiturate. Various measurements were made of the efficacy of the implants, and the mineral/collagen mixture, with or without marrow, was found to be effective in grafting.

The foregoing examples provide specific embodiments of the present invention, other embodiments being readily within the skill of the art. Thus, the scope of the present invention is defined by the following claims without limitation to the foregoing examples.

We claim:

1. A conductive bone-repair composition which contains a mixture consisting essentially of about 87 to 91% calcium phosphate particulate mineral component, said mineral component being a mixture of about 60% hydroxyapatite and about 40% tricalcium phosphate, in admixture with about 9 to 13% of atelopeptide reconstituted fibrillar collagen, said composition is prepared by a process comprising the steps of:

mixing a liquid dispersion of said collagen with the mineral component in dry particulate form, followed by molding and drying the composition in the mold to obtain a dried composition.

* * * * *